United States Patent [19]

Isenberg

[11] 4,285,790
[45] Aug. 25, 1981

[54] SENSOR FOR OXYGEN-COMBUSTIBLES GAS MIXTURES

[75] Inventor: Arnold O. Isenberg, Forest Hills, Pa.

[73] Assignee: Westinghouse Electric Corp., Pittsburgh, Pa.

[21] Appl. No.: 132,197

[22] Filed: Mar. 20, 1980

[51] Int. Cl.³ .................. G01N 27/56; G01N 27/58
[52] U.S. Cl. .................. 204/195 R; 204/195 S
[58] Field of Search .......... 204/1 Y, 1 S, 1 K, 195 R, 204/195 S; 429/16, 46

[56] References Cited

U.S. PATENT DOCUMENTS

| 3,268,365 | 8/1966 | McQuade et al. | 429/16 |
| 3,466,197 | 9/1969 | Bawa | 429/46 |
| 4,080,487 | 3/1978 | Reiser | 429/16 |

FOREIGN PATENT DOCUMENTS

694860  9/1964  Canada .................... 429/46

OTHER PUBLICATIONS

A. N. Webb et al., J. Electrochem. Soc., vol. 112, No. 11, pp. 1059–1063, (1965).

Primary Examiner—G. L. Kaplan
Attorney, Agent, or Firm—M. P. Lynch

[57] ABSTRACT

A molten carbonate electrochemical cell operating at a temperature between 400° and 700° C. is used to remove $O_2$ in combination with $CO_2$ from an oxygen/combustibles gas mixture to provide a low temperature measurement of the oxygen content of the gas mixture.

8 Claims, 2 Drawing Figures

SENSOR FOR OXYGEN-COMBUSTIBLES GAS MIXTURES

BACKGROUND OF THE INVENTION

The quantitative measurement of oxygen in the presence of combustibles, such as hydrogen or carbon monoxide, is important.

Traditional gas analysis methods, such as gas chromotography, can be used, but these methods require gas sampling and do not provide the in-situ type of analysis that allows fast control of firing conditions to prevent hazardous conditions. Thus, it is preferred to use an in-situ probe-type sensor for monitoring these potentially explosive conditions.

Conventional electrochemical potential measurements of commercially available probe-type solid electrolyte sensors are undesirable for this gas measuring application in that such devices operate at temperatures, i.e. 800°-1200° C., at which undesirable reactions occur between the oxygen and fuel constituents of a gas mixture.

SUMMARY OF THE INVENTION

There is disclosed herein with reference to the accompanying drawings an electrochemical cell device which separates oxygen and combustibles at a relatively low temperature and allows the measurement of the separated components without encountering undesirable reactions.

The successful operation of the device requires the presence of carbon dioxide or carbon dioxide and water vapor in the gas mixture. The device consists of a molten carbonate electrochemical cell that operates at a temperature of approximately 450° C. to 700° C. to separate oxygen from the combustibles constituents of the gas mixture and produce a cell current indicative of the oxygen content of the gas mixture. The gross combustibles content of the gas mixture is then measured.

DESCRIPTION OF THE DRAWINGS

The invention will become more readily apparent from the following exemplary description in connection with the accompanying drawings.

DESCRIPTION OF THE PREFERRED EMBODIMENT

Figure 1:
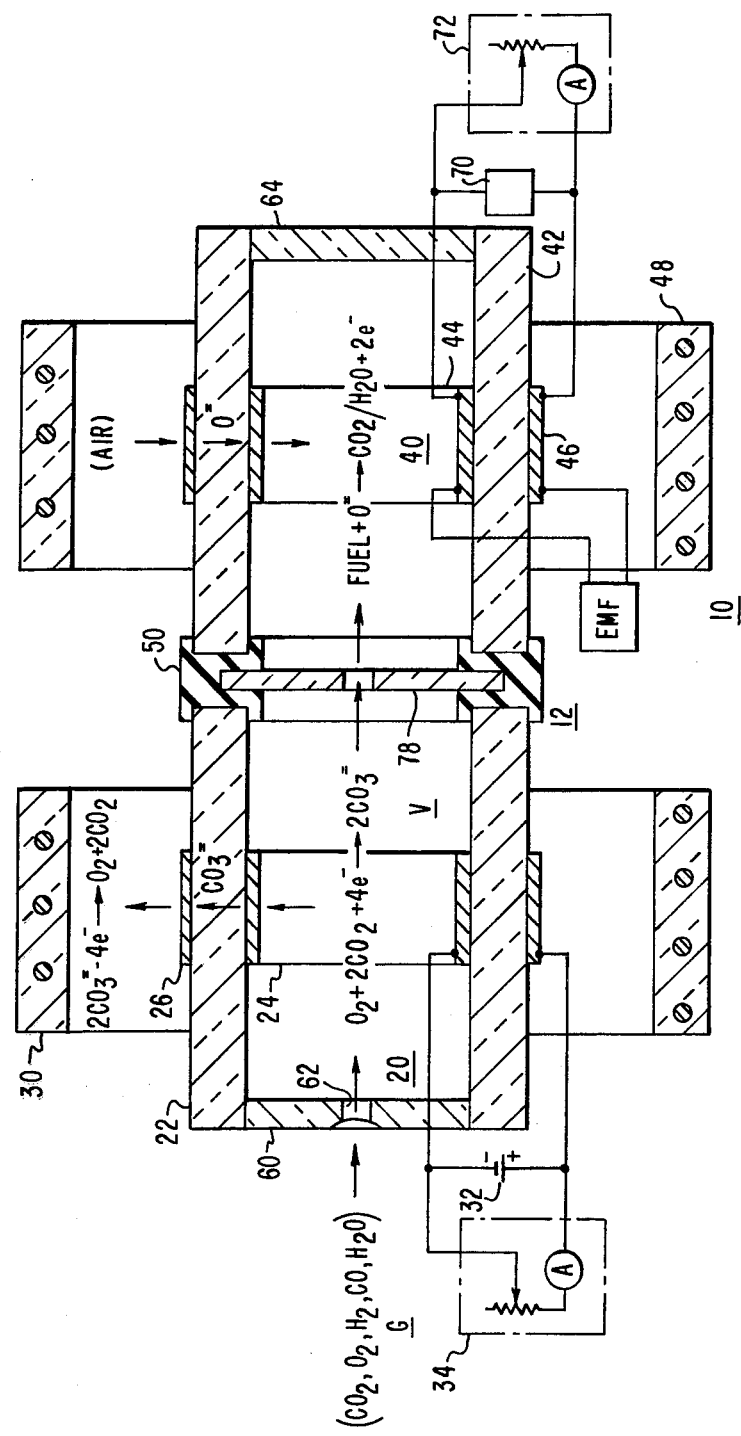
FIG. 1 is a section pictorial illustration of an embodiment of the invention.

Referring to FIG. 1 there is illustrated in section a gas constituent separating and measuring device 10. The typical embodiment of the device 10 as shown in FIG. 1 consists of a tubular enclosure 12 consisting of a tubular molten carbonate electrochemical cell 20 and a tubular oxygen ion conductive solid electrolyte electrochemical cell 40 secured in an end-to-end relationship by a seal member 50. A gas diffusion limiting adapter, or orifice plate, 60 is positioned in one end of the tubular enclosure 12 to accommodate the diffusion of the constituents, i.e., $CO_2$, $O_2$, $H_2$, CO, etc. from an oxygen/combustibles gas environment G through the aperture 62 into the internal volume V of the tubular enclosure 12. The opposite end of the tubular enclosure 12 is closed by the end plate 64. The molten carbonate electrochemical cell 10 consists of a molten carbonate electrolyte 22 and electrodes 24 and 26 disposed on opposite surfaces thereof. The oxygen ion conductive solid electrolyte electrochemical cell 40 consists of an oxygen ion conductive solid electrolyte member 42 and electrodes 44 and 46 disposed on opposite surfaces thereof. The seal 50 is of a material suitable for withstanding the mechanical vibration and temperature of operation of the device 10.

The molten carbonate electrochemical cell 20 is operated at a temperature in a range between approximately 400° C. and 700° C. which is maintained by the furnace 30 within which the cell 20 is positioned. The oxygen ion conductivity operation of the cell 40, necessitates an operating temperature between 700° C. and 1200° C., which is established and maintained by the furnace 48 within which the cell 40 is positioned. The cell 40 typically consists of a solid electrolyte material consisting of stabilized zirconia, and electrodes 44 and 46 of platinum. The composition and operation of the oxygen ion conductive cell 40 is well known in the art, and is typically described and illustrated in U.S. Pat. No. Re. 28,792 which is assigned to the assignee of the present invention and incorporated herein by reference.

The molten carbonate electrolyte 22 of the cell 20 consists of a eutectic carbonate mixture impregnated in a porous mechanical support of a suitable non-reactive ceramic, such as lithium aluminate. Suitable eutectic carbonate mixtures include mixtures of $Li_2CO_3$, $K_2CO_3$, $Na_2CO_3$ and $Cs_2CO_3$ which melt at temperatures below 500° C. and exhibit high $CO_3^{--}$ conductivity. The electrodes 24 and 26 are non-catalytic electrodes constructed of noble metals or conducting oxides such as lithiated nickel oxide or silver, copper oxide or magnetite.

The constituents of the monitored gas environment G, which is assumed to include $CO_2$, or a combination of $CO_2$ and water vapor, in excess of $O_2$, and constituents such as CO and $H_2$, as would typically be present in a combustion process, enter initially that portion of the volume V within the molten carbonate electrochemical cell 20. Under the influence of a voltage of up to 1.5 volts of the polarity indicated applied to the electrodes 24 and 26 of the molten carbonate cell 20 by the voltage source 32, the total oxygen content in the gas mixture present within the tubular cell 20 is transported through the molten carbonate electrolyte 22 by an equivalent amount of $CO_2$ in accordance with the following reaction at the cathode electrode 24:

$$2CO_2 + O_2 + 4e^- \rightarrow 2CO_3^{--} \tag{1}$$

and oxygen will be released at the anode electrode 26 by the reaction:

$$2CO_3^{==} 4 \rightarrow O_2 + 2CO_2 \tag{2}$$

A current measuring circuit 34 connected to the electrodes 24 and 26 measures the current developed by the molten carbonate cell 20 in response to the transfer of oxygen by the carbon dioxide via carbonate ions as an indication of the oxygen concentration in the monitored gas environment G.

In the event water vapor is present in the gas mixture and hydroxides accumulate in the molten carbonate electrolyte 22, hydroxide carbonate mixtures can develop as the water vapor can transfer oxygen through the electrolyte via hydroxyl ions.

The molten carbonate electrolyte 22 effectively supports the transfer of $O_2$ with $CO_2$ from the internal volume in response to the applied potential from the voltage source 32 at operating temperatures of between approximately 400° and 700° C. as controlled by the furnace 30. This low temperature of operation of the molten carbonate cell 20 avoids the possibility of initiating a chemical reaction between the fuel and oxygen constituents of the monitored gas environment entering the device 10 prior to the removal or separation of the oxygen constituent from the gas mixture entering the device 10 through the aperture 62. The combustibles constituent(s), i.e. $H_2$, is then transported to the portion of the internal volume V of the device 10 enclosed by the oxygen ion conductive solid electrolyte cell 40. A voltage source 70 is connected across the electrodes 44 and 46 to maintain a flow of oxygen from an external oxygen source, such as air, through the solid electrolyte member 42 into the volume enclosed by the cell 40 to combustively react with the fuel constituent in the presence of a catalytic electrode 44, which is typically platinum, at the operating temperature of the cell 40 which is typically in excess of 800° C. The cell current generated by the transport of the oxygen ions, is measured by the current measuring circuit 72 as an indication of the gross combustibles content of the monitored gas environment G.

While the voltage source 70 provides a means for maintaining a steady applied potential, the self-generated EMF of the cell 40 resulting from the oxygen differential partial pressure across the electrolyte 42 can be employed to effect the desired transfer of oxygen to combustibly react with the fuel constituents of the gas mixture at the catalytic electrode 44.

It is apparent that the device 10 of FIG. 1 can consist solely of the molten carbonate cell 20 if only an oxygen measurement is required.

In the alternative, an EMF measuring circuit can be connected across the electrodes 44 and 46 of the cell 40, as described in the above-identified reissue patent, to provide an oxygen measurement in accordance with the well-known Nernst equation, assuming a known or steady oxygen reference, such as air, at the electrode 46. This well-known technique for providing an oxygen measurement can indirectly provide a measure of the concentration of combustibles inasmuch as the low temperature oxygen concentration measured by the molten carbonate cell 20 will differ from that measured by the high temperature operation solid electrolyte cell 40 by the amount of oxygen that is consumed by the presence of combustibles at the elevated operating temperature of the cell 40.

An optional gas diffusion aperture element, or orifice plate, 78 can be employed between the internal volumes of the device 10 defined by the cells 20 and 40 to provide a range selection control by limiting the amount of gas composition entering the cell 40.

Figure 2:
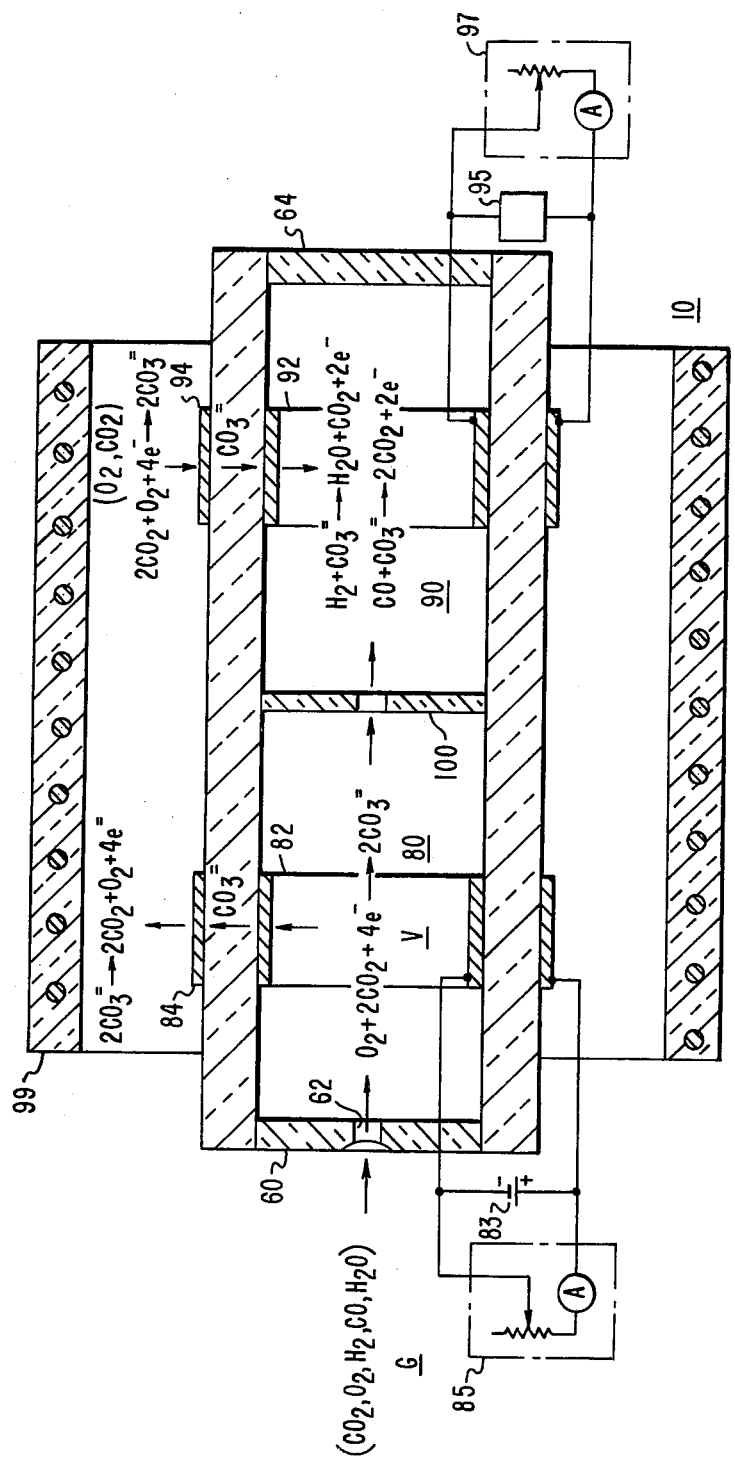
FIG. 2 is a section pictorial illustration of an alternate embodiment of the invention.

Referring to FIG. 2, there is illustrated in a sectioned schematic form an alternate embodiment which eliminates the need for the high temperature oxygen ion conductive electrochemical cell 40 of FIG. 1 and employs two molten carbonate electrochemical cells 80 and 90 which share a single furnace 99 which maintains the two cells at a common operating temperature of between 400° C. and 700° C. The configuration of FIG. 2 eliminates the separate heating levels of the embodiment of FIG. 1 and further eliminates the need for the sealing means 50. In the implementation of the device 10 of FIG. 2 the oxygen and combustibles content of the gas mixture are measured by the dual molten carbonate cell combination of cells 80 and 90 which may consist of separate electrolytes or share a single common molten carbonate electrolyte 82. The gas mixture passing through the aperture 62 of the gas diffusion limiting adapter 60 first enters the internal volume defined by the tubular molten carbonate electrochemical cell 80. As described above with reference to the operation of the molten carbonate cell 20 of FIG. 1, the cell 80 responds to the applied potential from source 83 to the non-catalytic electrodes 82 and 84 by transporting $CO_2$ and a corresponding amount of $O_2$ from the internal volume through the electrolyte 88 in accordance with equation (1) above. The current developed by the cell 80, and measured by the current measuring circuit 85 is a measurement of the oxygen concentration of the gas mixture diffusing through the aperture 62. The non-catalytic electrodes 82 and 84 of the cell 80 may be constructed from copper, nickel, cobalt, silver, gold and electronically conducting metal oxides except the oxides of the platinum group elements.

The combustibles constituent(s) remaining following the removal of the oxygen by the operation of the cell 80 enter the internal volume defined by the molten carbonate cell 90. The electrodes 92 and 94 are catalytic electrodes, i.e., typically platinum. The oxygen reference environment of cell 40 of FIG. 1 is replaced by an external gas mixture of $O_2$ and $CO_2$ surrounding the cell 90 and in contact with the electrode 94. The electrical potential of the polarity shown is applied across electrodes 94 and 96 by the voltage source 95 to produce a transport of $CO_2$ and an equivalent amount of $O_2$ through the molten carbonate electrolyte 88 to the internal volume of the device 10 defined by the cell 90. The introduction of oxygen to this internal volume to contact the combustible content present at the surface of the catalytic electrode 92 results in the electrochemical combustion of the combustible or fuel constituent(s) within the volume of the cell 90. The current produced by the cell 90, as measured by the current measurement circuit 97 is an indication of the gross combustibles content of the gas mixture entering the diffusion orifice 62.

As discussed above with reference to the voltage source 70 of FIG. 1, the voltage source 95 can be eliminated and the self-generated EMF of the cell 90 employed to transfer $O_2$ to combustibly react with the fuel constituents of the catalytic electrode 92.

As discussed above with reference to the embodiment of FIG. 1, an optional gas diffusion limiting aperture adapter 100 can be inserted to partition the internal volumes defined by the cells 80 and 90, respectively, to provide capability of range selection by limiting the fuel constituent gas mixture entering the volume defined by the cell 90.

I claim:

1. An oxygen sensor apparatus for measuring the oxygen content of an oxygen/combustibles gas mixture wherein said gas mixture includes $CO_2$, or the combination of $CO_2$ and water vapor, in excess of $O_2$, comprising:

a molten carbonate electrochemical cell including a molten carbonate electrolyte consisting of a eutectic carbonate mixture impregnated in a porous support and first and second electrodes disposed on opposite surfaces of said molten carbonate electrolyte;

means for supplying an oxygen/combustibles gas mixture containing $CO_2$, or the combination of $CO_2$ and water vapor, in excess $O_2$ in contact with the first electrode surface of said molten carbonate electrolyte, said first electrode being a non-catalytic electrode;

means for transporting $CO_2$ and a corresponding amount of $O_2$ from said gas mixture through said molten carbonate electrolyte to the second electrode surface of said molten carbonate electrolyte to deplete the oxygen present in said gas mixture, said transport of $CO_2$ and $O_2$ producing a molten carbonate electrochemical cell current; and means for measuring said cell current as an indication of the oxygen content of said gas mixture.

2. A sensor apparatus as claimed in claim 1 further including means for heating said molten carbonate electrochemical cell to a temperature to enhance the conductivity of said molten carbonate cell while limiting said temperature to a level less than that at which a combustible reaction would occur between the oxygen and combustibles constituents of said gas mixture.

3. A sensor apparatus as claimed in claim 1 wherein said eutectic carbonate mixture comprising said molten carbonate electrolyte is a mixture selected from the following: $Li_2CO_3$, $K_2CO_3$, $Na_2CO_3$, and $Cs_2CO_3$.

4. A gas sensor apparatus for measuring the gross combustibles content of an oxygen/combustibles gas mixture wherein said gas mixture includes $CO_2$, or the combination of $CO_2$ and water vapor, in excess of $O_2$, comprising:

a molten carbonate electrochemical cell including a molten carbonate electrolyte consisting of a eutectic carbonate mixture impregnated in a porous support and first and second electrodes disposed on opposite surfaces of said molten carbonate electrolyte, said first electrode being a non-catalytic electrode;

means for supplying an oxygen/combustibles gas mixture containing $CO_2$, or the combination of $CO_2$ and water vapor, in excess $O_2$ in contact with the first electrode surface of said molten carbonate electrolyte;

means for transporting $CO_2$ and a corresponding amount of $O_2$ from said gas mixture through said molten carbonate electrolyte to the second electrode surface of said molten carbonate electrolyte to deplete the oxygen present in said gas mixture, said transport of $CO_2$ and $O_2$ producing a molten carbonate electrochemical cell current;

a second electrochemical cell means including an electrolyte and first and second electrodes disposed on opposite surfaces thereof, said first electrode being a catalytic electrode, the gas mixture absent the oxygen content which was depleted by said molten carbonate electrochemical cell contacting said first electrode of said second electrochemical cell, an oxygen gas environment contacting said second electrode of said second electrochemical cell, means for transporting oxygen from said oxygen gas environment to the first electrode surface of said second electrochemical cell, said first electrode being a catalytic electrode causing an electrochemical combustible reaction between the oxygen and the combustible constituents of said gas mixture at said first electrode, the transport of said oxygen producing a cell current in said second electrochemical cell means, and means for measuring the cell current of said second electrochemical cell as an indication of the gross combustibles content of the oxygen/combustible gas mixture.

5. A gas sensor apparatus as claimed in claim 4 wherein said second electrochemical cell is a molten carbonate electrochemical cell, said oxygen gas environment contacting said second electrode including $CO_2$, said means for applying a voltage across the electrodes of said second electrochemical cell means transporting $CO_2$ and a corresponding amount of $O_2$ through said molten carbonate electrochemical cell to said first electrode.

6. A sensor apparatus as claimed in claim 5 wherein said eutectic carbonate mixture comprising said molten carbonate electrolyte is a mixture selected from the following: $Li_2CO_3$, $K_2CO_3$, $Na_2CO_3$, and $Cs_2CO_3$.

7. A gas sensor apparatus as claimed in claim 4, further including means for measuring the cell current of said molten carbonate electrochemical cell as an indication of the oxygen content of the oxygen/combustibles gas mixture.

8. A gas sensor apparatus for measuring the gross combustibles content of an oxygen/combustibles gas mixture wherein said gas mixture includes $CO_2$ or the combination of $CO_2$ and water vapor, in excess of $O_2$, comprising:

a molten carbonate electrochemical cell including a molten carbonate electrolyte consisting of a eutectic carbonate mixture impregnated in a porous support and first and second electrodes disposed on opposite surfaces of said molten carbonate electrolyte, said first electrode being a non-catalytic electrode;

means for supplying an oxygen combustibles gas mixture containing $CO_2$, or the combination of $CO_2$ and water vapor, in excess of $O_2$ in contact with the first electrode surface of said molten carbonate electrolyte;

means for transporting $CO_2$ and a corresponding amount of $O_2$ from said gas mixture through said molten carbonate electrolyte to the second electrode surface of said molten carbonate electrolyte to deplete the oxygen present in said gas mixture;

a second electrochemical cell means including an electrolyte and first and second electrodes disposed on opposite surfaces thereof, said first electrode being a catalytic electrode, the gas mixture absent the oxygen content which was depleted by said molten carbonate electrochemical cell contacting said first electrode of said second electrochemical cell, an oxygen gas environment contacting said second electrode of said second electrochemical cell;

means for transporting oxygen from said oxygen gas environment to the first electrode surface of said second electrochemical cell, said first electrode being a catalytic electrode causing an electrochemical combustible reaction between the oxygen and the combustible constituents of said gas mixture at said first electrode, the transport of said oxygen producing a cell current in said second electrochemical cell means, said second electrochemical cell being an oxygen ion conductive solid electrolyte electrochemical cell, said means for transporting consisting of a voltage source connected across the electrodes of said second electrochemical cell to pump oxygen from said oxygen gas environment to said first electrode; and means for measuring the cell current of said second electrochemical cell as an indication of the gross combustibles content of the oxygen/combustibles gas mixture.

* * * * *